(12) United States Patent
Hartley et al.

(10) Patent No.: US 8,475,514 B2
(45) Date of Patent: Jul. 2, 2013

(54) DEPLOYMENT DEVICE

(75) Inventors: David Ernest Hartley, Western (AU); Werner Dieter Ducke, Western Australia (AU)

(73) Assignee: Cook Medical Technologies LLC, Bloomington, IN (US)

( * ) Notice: Subject to any disclaimer, the term of this patent is extended or adjusted under 35 U.S.C. 154(b) by 306 days.

(21) Appl. No.: 12/671,177

(22) PCT Filed: Aug. 13, 2008

(86) PCT No.: PCT/US2008/009685
§ 371 (c)(1),
(2), (4) Date: Jun. 2, 2010

(87) PCT Pub. No.: WO2009/023221
PCT Pub. Date: Feb. 19, 2009

(65) Prior Publication Data
US 2010/0274340 A1    Oct. 28, 2010

Related U.S. Application Data

(60) Provisional application No. 60/964,456, filed on Aug. 13, 2007.

(51) Int. Cl.
*A61F 2/06* (2006.01)
(52) U.S. Cl.
USPC .......................................................... 623/1.11
(58) Field of Classification Search
USPC ................ 623/1.11–1.12, 1.23; 606/108, 194
See application file for complete search history.

(56) References Cited

U.S. PATENT DOCUMENTS 4,921,484 A * 5/1990 Hillstead ....................... 604/104
5,776,142 A   7/1998 Gunderson (Continued)

FOREIGN PATENT DOCUMENTS

EP   1 358 903 A   11/2003
EP   1 369 098 A   12/2003

(Continued)

OTHER PUBLICATIONS

International Search Report in International Application No. PCT/US2008/009685, dated Nov. 28, 2008, 7 pages.

(Continued)

*Primary Examiner* — Gary Jackson
*Assistant Examiner* — Amy Shipley
(74) *Attorney, Agent, or Firm* — Brinks, Hofer, Gilson & Lione

(57) ABSTRACT

A stent graft deployment device (10) has a tubular fixed handle (34, 36) to be gripped and held by a user and an elongate release handle (30) extending through the fixed handle so that the release handle can be moved through the fixed handle. The deployment device assembly has a pusher (38) and a sheath (18) to cover a stent graft (64) on the pusher. The pusher is connected to the fixed handle and the sheath is connected to the release handle so that retraction of the release handle through the fixed handle causes the sheath to be retracted from the stent graft on the pusher. The fixed handle includes a grip component (34) that grips the pusher and a rotator component (36) that grips a release clamp (48) on the pusher. The release clamp has trigger wires for the release of the stent graft attached to it. The rotator component has a screw thread (54) with a portion (52) of the release clamp engaged into the screw thread so that rotation of the rotator component causes longitudinal movement of the release clamp on the pusher which pulls the trigger wires.

20 Claims, 7 Drawing Sheets

U.S. PATENT DOCUMENTS

| | | |
|---|---|---|
| 6,533,881 B1 | 3/2003 | Wall |
| 6,939,370 B2 * | 9/2005 | Hartley et al. ............... 623/1.11 |
| 8,043,354 B2 * | 10/2011 | Greenberg et al. .......... 623/1.12 |
| 2005/0049667 A1 | 3/2005 | Arbefeuille et al. |
| 2007/0260301 A1 * | 11/2007 | Chuter et al. ................ 623/1.11 |
| 2008/0082154 A1 * | 4/2008 | Tseng et al. ................. 623/1.11 |
| 2009/0030495 A1 * | 1/2009 | Koch ............................ 623/1.11 |

FOREIGN PATENT DOCUMENTS

| | | |
|---|---|---|
| WO | WO 2006/007389 A | 1/2006 |
| WO | WO 2006/071915 A | 7/2006 |
| WO | WO 2007/127351 A | 11/2007 |
| WO | WO 2009/023221 A1 | 2/2009 |

OTHER PUBLICATIONS

Written Opinion in International Application No. PCT/US2008/009685, dated Nov. 28, 2008, 14 pages.

* cited by examiner

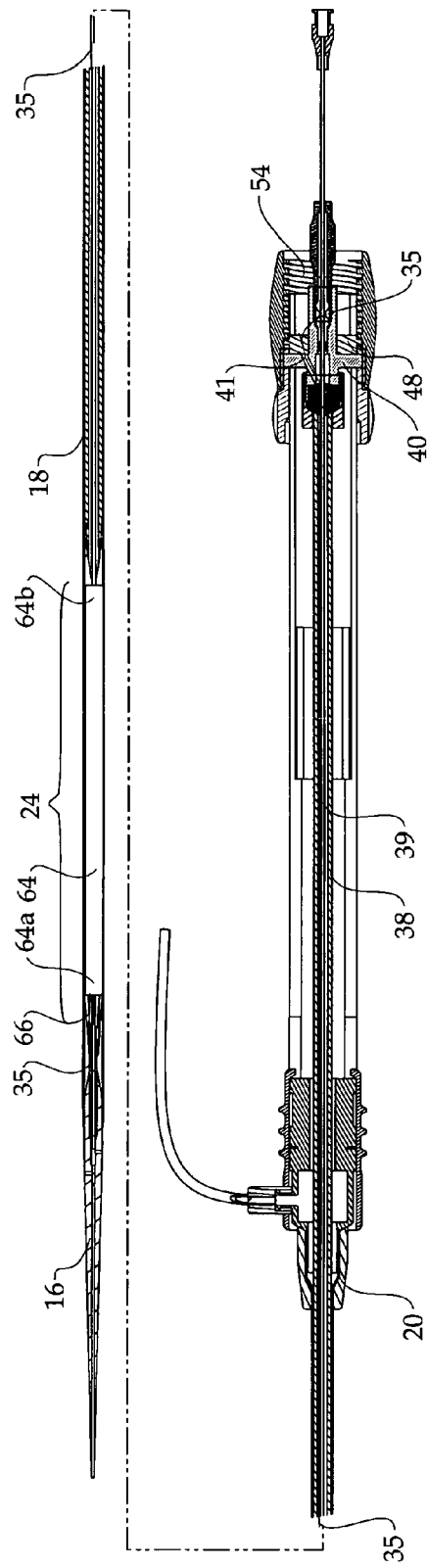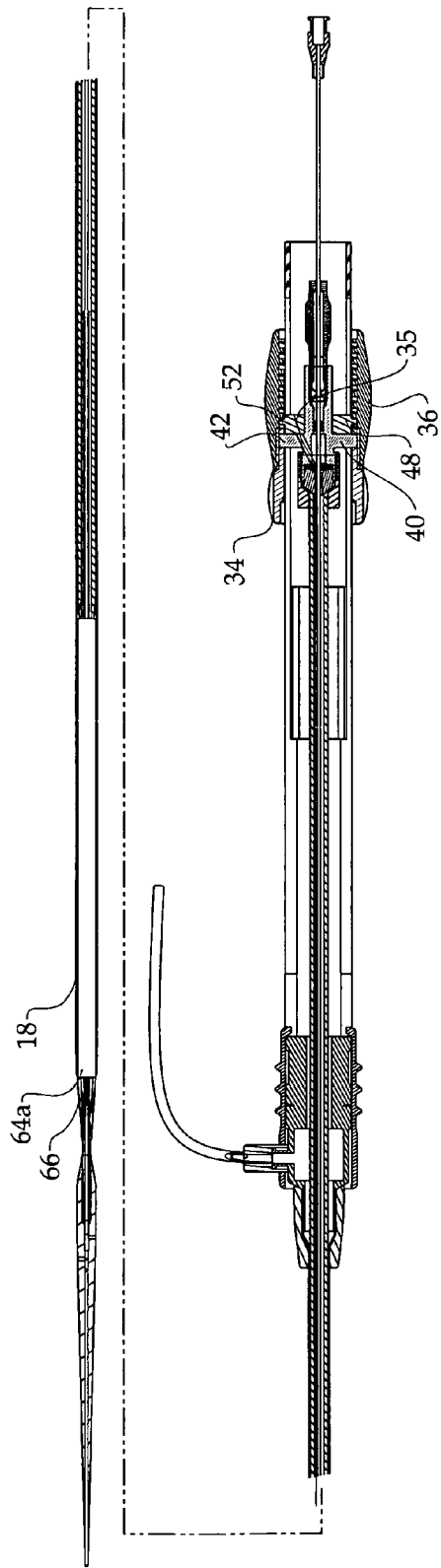

DEPLOYMENT DEVICE

This application is a National Stage of International Application PCT/US2008/009685 filed with the U.S.P.T.O. on Aug. 13, 2008, which claims priority to U.S. Provisional Pat. No. 60/964,456, filed Aug. 13, 2007, the entirety of which is hereby incorporated by reference.

TECHNICAL FIELD

This invention relates to a deployment device, and more particularly to a device for controlled endovascular deployment of a stent graft.

BACKGROUND OF THE INVENTION

In PCT Patent Publication No. WO 98/53761 entitled "A Prosthesis and a Method Deploying a Prosthesis" to the present applicant there is disclosed an introducer for a stent graft which retains the stent graft so that each end can be moved and released independently during the process of endovascular deployment of the stent graft. This device requires that a number of actions be taken in a particular consecutive order to place a stent graft in the required position in the vasculature. One end of the stent graft is released and then another end, and if required, between the release of each of the ends, a branch stent graft is placed into a side arm of the stent graft. These features and other features disclosed in PCT Patent Publication No. WO 98/53761 are incorporated herein by reference in their entirety into this specification.

It is desirable that the set of sequential actions necessary to release the stent graft at the desired position in the vasculature be undertaken in the required order and that there be less chance for operator error during such a deployment.

SUMMARY OF THE INVENTION

It is the object of this invention therefore to provide a deployment device which is arranged to introduce, deploy and release a stent graft by a series of sequential actions.

According to a first aspect of the present invention, there is provided a stent graft deployment device including a handle, the handle including a first part to be gripped and held by a user and a second part to be moved relative to the first part; a pusher on which a stent graft may be mounted; and a sheath to cover a stent graft on the pusher; wherein the pusher is connected to the first part of the handle and the sheath is connected to the second part of the handle, whereby retraction of the first part of the handle with respect to the second part of the handle causes the sheath to be retracted from a stent graft on the pusher.

According to a first aspect of the present invention, there is provided a stent graft deployment device including a handle, the handle including a first part to be gripped and held by a user and a second part to be moved relative to the first part; a pusher on which a stent graft may be mounted; and a sheath to cover a stent graft on the pusher; wherein the pusher is connected to the first part of the handle and the sheath is connected to the second part of the handle, whereby retraction of the first part of the handle with respect to the second part of the handle causes the sheath to be retracted from a stent graft on the pusher.

Preferably the first part includes a first component which grips the pusher and a second component which grips a release clamp on the pusher, the release clamp on the pusher having trigger wires for the release of the stent graft from the pusher assembly attached thereto, whereby movement of the second component with respect to the first moves the release clamp on the pusher and thereby pulls the trigger wires.

Preferably the second component rotates with respect to the first component and the second component includes a screw thread with a portion of the release clamp engaged into the screw thread whereby rotational movement of the second part causes longitudinal movement of the release clamp on the pusher.

The device can further include a stop on the first part, the stop arranged to engage the release clamp on the pusher assembly after a selected amount of movement of the first part has occurred whereby to prevent further retraction of the sheath from the stent graft until the release clamp has been moved by rotation of the second component on the second part.

The first part can include a bayonet socket for a hub of the sheath.

Preferably the second part is substantially cylindrical and the first part is tubular and slides within the second part.

Preferably the tubular first part has longitudinal slots and an internal lumen and the pusher extends within the longitudinal lumen and the pusher includes arms which extend through the longitudinal slots to engage with the second part whereby the first part can be moved with respect to the second part.

The device can further include a first stop to prevent the first part from moving through the second part in a reverse direction.

The device can further include a detent arrangement acting between the first component and the second component to allow rotation of the second component only in a selected direction.

According to a second aspect of the present invention, there is provided a stent graft deployment device, the device including a tubular fixed handle to be gripped and held by a user and an elongate release handle extending through the fixed handle whereby the release handle can be moved through the fixed handle, the deployment device further including a pusher and a sheath to cover a stent graft on the pusher, the pusher being connected to the fixed handle and the sheath being connected to the release handle whereby retraction of the release handle through the fixed handle causes the sheath to be retracted from the stent graft on the pusher.

According to a third aspect of the present invention, there is provided a stent graft deployment device including: a handle, the handle including a tubular fixed handle to be gripped and held by a user and an elongate release handle extending through the fixed handle whereby the release handle can be moved through the fixed handle; a pusher and a sheath to cover a stent graft on the pusher, the pusher being connected to the fixed handle and the sheath being connected to the release handle, whereby retraction of the release handle through the fixed handle causes the sheath to be retracted from a stent graft on the pusher; the fixed handle including a grip component that grips the pusher and a rotator component that grips a release clamp on the pusher; the release clamp on the pusher having a trigger wire for the release of a stent graft from the pusher, attached thereto; and the rotator component including a screw thread with a portion of the release clamp engaged into the screw thread, whereby rotational movement of the rotator component causes longitudinal movement of the release clamp on the pusher thereby to pull the trigger wires.

According to a fourth aspect of the present invention, there is provided an assembly of a stent graft deployment device as described above and a stent graft mounted on the pusher.

According to a fifth aspect of the present invention, there is provided an assembly of a handle, a stent graft deployment device and a stent graft, the handle including a first part to be gripped and held by a user and a second part to be moved relative to the first part, the deployment device including a pusher assembly, the stent graft being mounted onto the pusher assembly and a sheath to cover the stent graft on the pusher assembly, the pusher assembly being connected to the first part and the sheath being connected to the second part whereby retraction of the first part with respect to the second part causes the sheath to be retracted from the stent graft on the pusher assembly.

According to a fifth aspect of the present invention, there is provided a deployment assembly comprising a handle, a stent graft deployment device and stent graft, the handle including a tubular fixed handle to be gripped and held by a user and an elongate release handle extending through the fixed handle whereby the release handle can be moved through the fixed handle, the stent graft deployment device including a pusher assembly and a sheath to cover the stent graft on the pusher assembly, the pusher assembly being connected to the fixed handle and the sheath being connected to the release handle whereby retraction of the release handle through the fixed handle causes the sheath to be retracted from the stent graft on the pusher assembly, the fixed handle including a grip component which grips the pusher and the rotator component which grips a release clamp on the pusher, the release clamp on the pusher having trigger wires for the release of the stent graft from the pusher assembly, attached thereto and the rotator component including a screw thread with a portion of the release clamp engaged into the screw thread whereby rotational movement of the rotator component causes longitudinal movement of the release clamp on the pusher thereby pulls the trigger wires.

It will be seen that by the various forms of this invention, a device is provided which by the action of holding one portion of the deployment device and moving another portion of the deployment device in a linear sliding motion, the various sequential actions necessary to release the stent graft can occur.

BRIEF DESCRIPTION OF THE DRAWING

Preferred embodiments of the invention are now described, by way of example only, with reference to the accompanying drawings, in which:

FIGS. 5 to 9 show the view a detailed longitudinal cross-sectional view of the embodiment of FIG. 1 at various stages of deployment.

DETAILED DESCRIPTION

Figure 1:
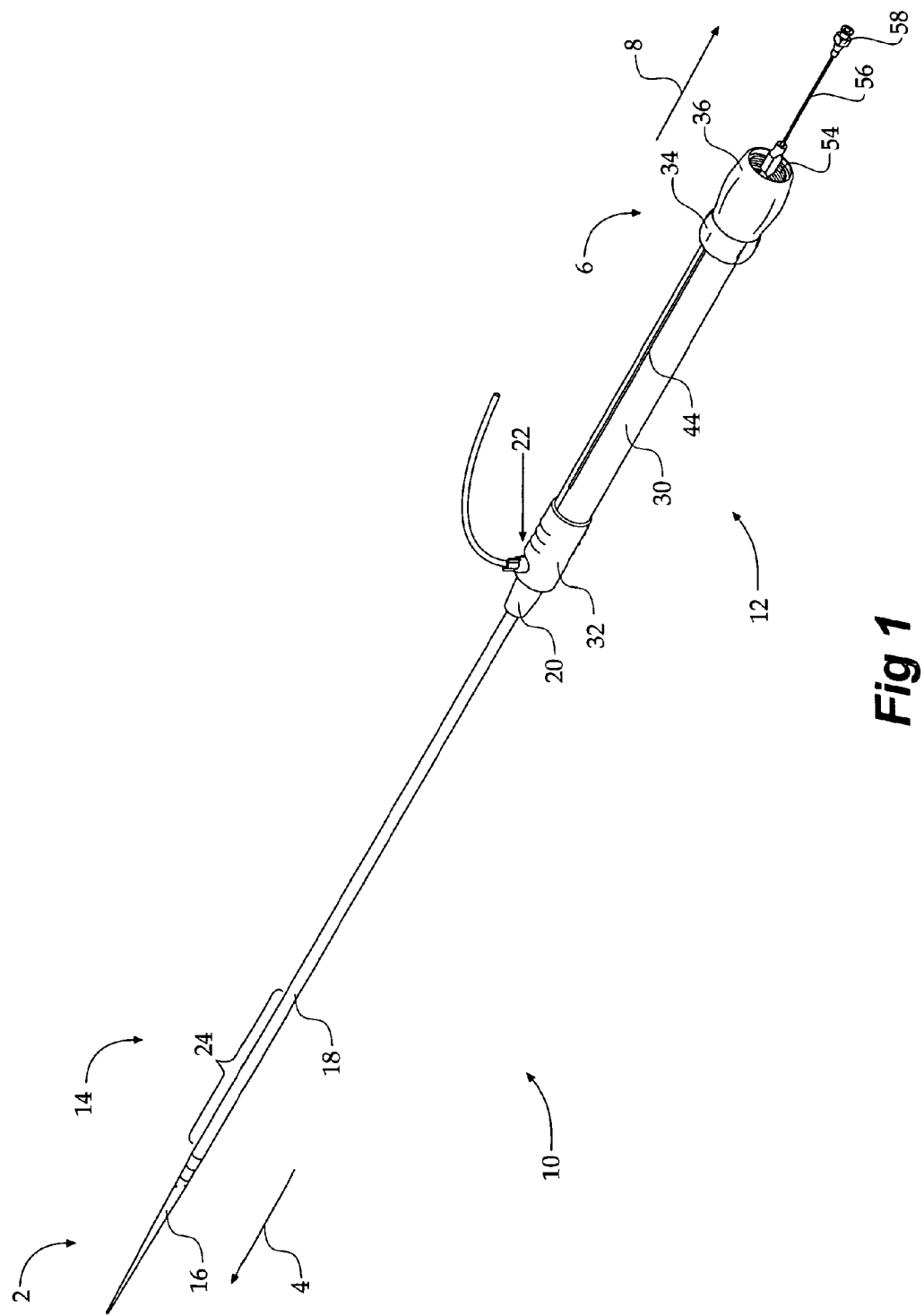
FIG. 1 shows a perspective view of a deployment device according to an embodiment of the present invention.

Throughout this discussion and as shown in FIG. 1 the term proximal means the end 2 of the handle and stent graft deployment device assembly 10 and the direction proximally is the direction shown by the arrow 4. The term distal means the end 6 of the handle and stent graft deployment device assembly 10 and the direction distally is the direction shown by the arrow 8.

Now looking more closely at the drawings it will be seen that the handle and stent graft deployment device assembly 10 includes a handle portion 12 and a stent graft delivery portion 14. The delivery portion 14 is arranged to be deployed within the vasculature of a patient by the Seldinger technique to deliver and release a stent graft within the vasculature, and the handle portion 12 remains outside the patient to be manipulated to deliver and release the stent graft.

The delivery portion 14 includes a nose cone dilator 16 and a sheath 18 extending from a sheath hub 20 which is engaged into the handle portion 12 with a bayonet type fitting 22. A stent graft is retained underneath the sheath 18 in the region 24 immediately distal of the nose cone dilator 16. The device is introduced into a patient over a guide wire (not shown) which passes through the guide wire catheter 56.

The handle assembly 12 comprises a release handle 30 which includes a proximal grip 32 and a fixed handle 34 to which is attached a rotator component 36.

Figure 2:
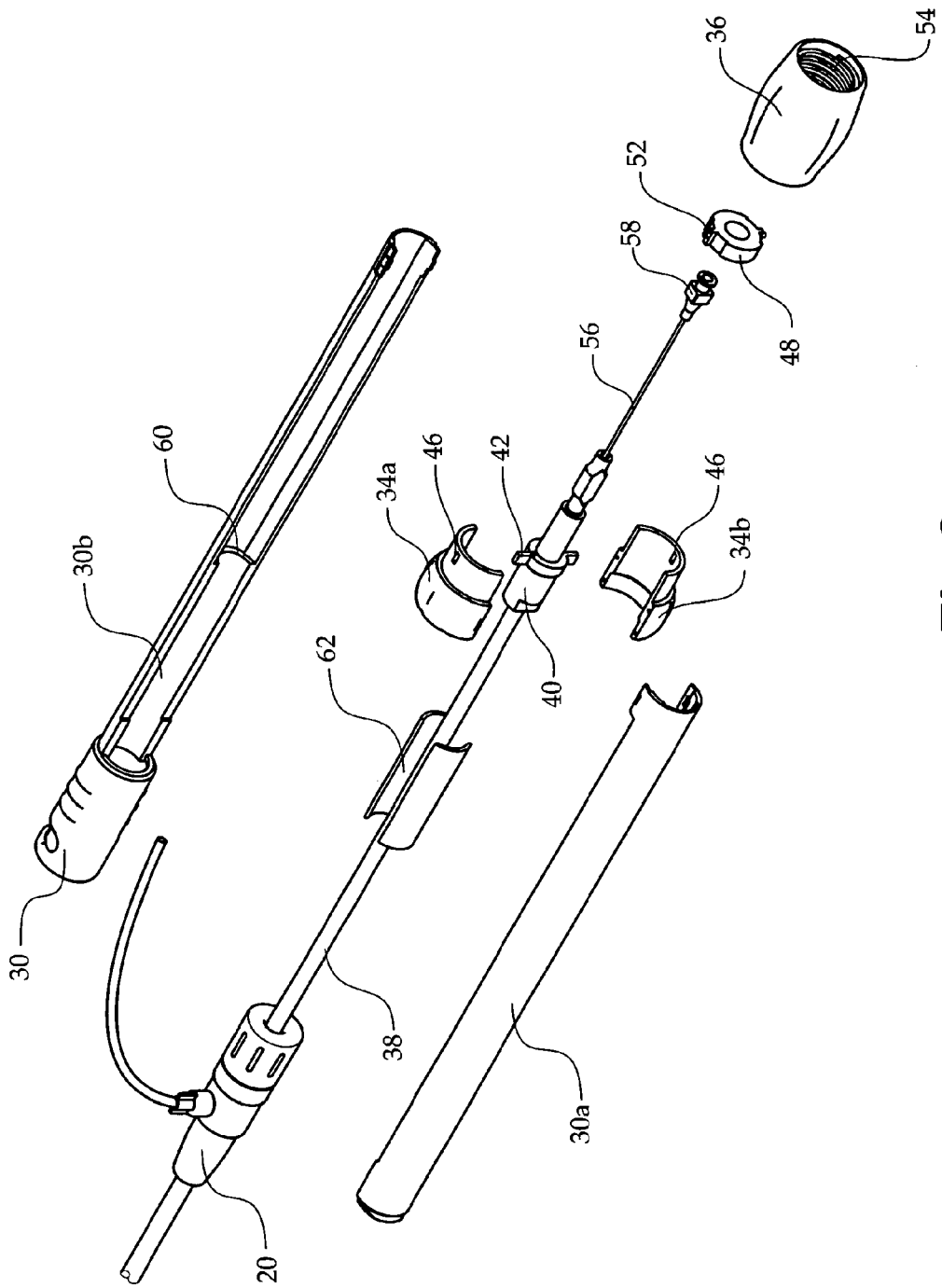
FIG. 2 shows an exploded view of the handle portion of the device shown in FIG. 1.

As can be seen in detail in FIG. 2 the release handle 30 is formed from semi-cylindrical release halves 30a and 30b which fit together around a pusher 38 for the stent graft delivery device.

The fixed handle 34 is also composed of fixed handle halves 34a and 34b which together fit around the release handle 30. The pusher 38 includes a pusher hub 40 which includes pins 42 extending diametrically in each direction from the hub 40 and through a slot 44 (as can be best seen in FIG. 1), that extends longitudinally along the release handle 30. The pins 42 engage into apertures 46 in the fixed handle halves 34a and 34b. The hub portion 40 also includes a release clamp 48 which slides along a portion 50 of the hub 40. The release clamp 48 includes pins 52 which extend diametrically through the slot 44 in the release handle 30 and engage into a screw thread 54 within the rotator component 36. The screw thread 54 can best be seen in FIGS. 1, 2 and 5 for instance.

Release or trigger wires 35 extend from each end of the stent graft 64 retained in the delivery device through a lumen 39 in the pusher 38 and a haemostatic seal within the pusher hub 40 and are fixed to the release clamp 48. The function of the release wires is discussed in more detail in relation to FIGS. 5 to 9.

The delivery device includes a guide wire catheter 56 and a syringe hub 58 at the distal end of the guide wire catheter 56. The guide wire catheter 56 extends through the pusher hub 40 and the lumen 39 within the pusher 38 to and through the nose cone dilator 16. The stent graft is retained concentrically around the guide wire catheter 56 immediately distal of the nose cone dilator 16.

The release handles are each substantially semi-cylindrical and when joined together form a tubular body and include inside and about half-way along their length a stepped shoulder 60 against which are engaged adjuster portions 62. The adjuster portions 62 are used to determine when the release of the stent graft has been achieved to a selected stage as will be discussed in relation to FIGS. 5 to 9.

Figure 3:
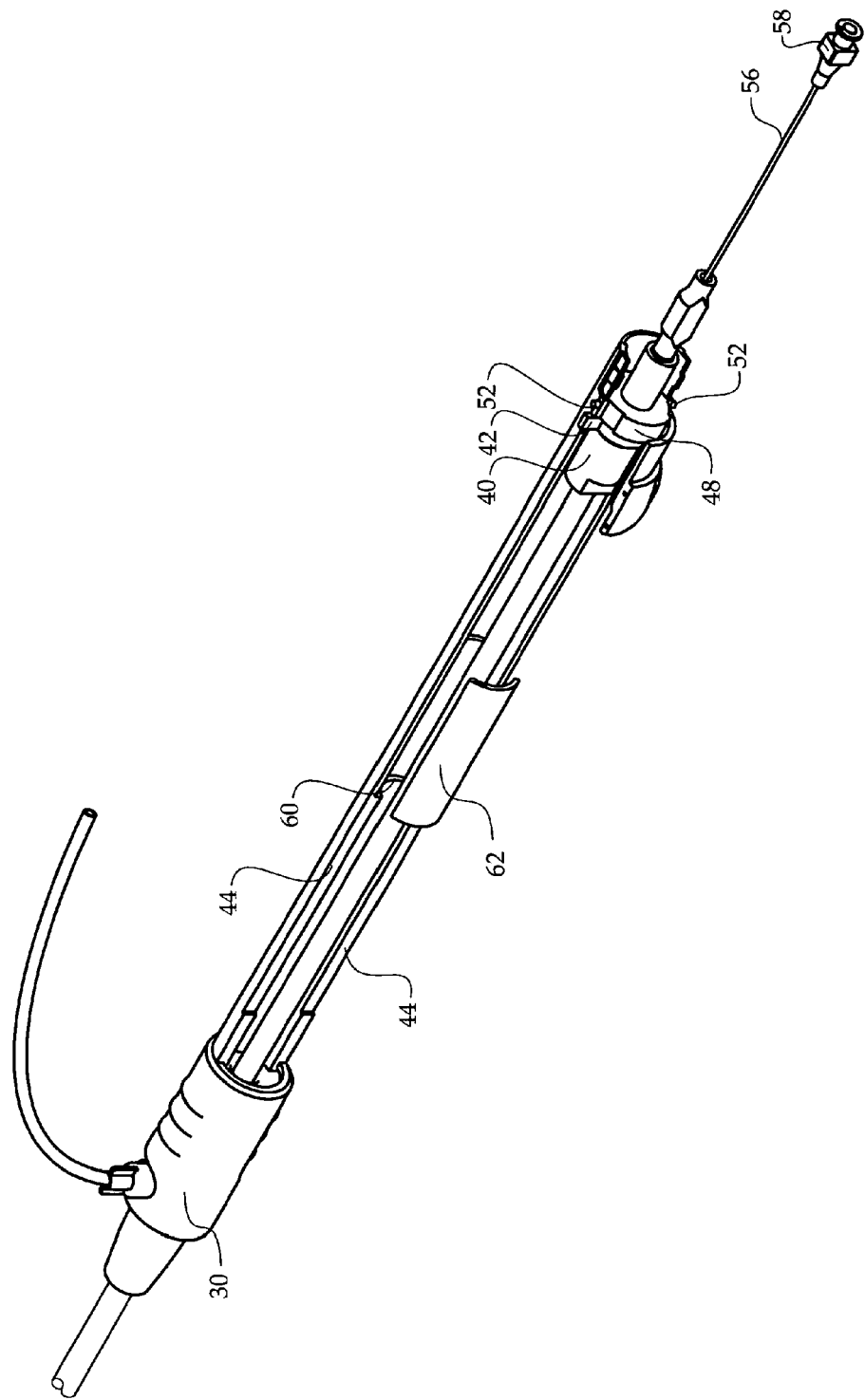
FIG. 3 shows an assembled and part cut away view of the handle portion of the device shown in FIG. 1.

FIG. 3 shows a cut-away assembled view of the handle portion of the delivery device. It can be particularly seen that the slot 44 in the release handle 30 is on both sides of the release handle and the stepped shoulder 60 has the adjusters 62 engaged against it. The rotator component 36 has been omitted from FIG. 3 so that the pusher hub 40 and pins 42 on the pusher hub 40 and the pins 52 on the release clamp 48 can be easily seen.

Figure 4:
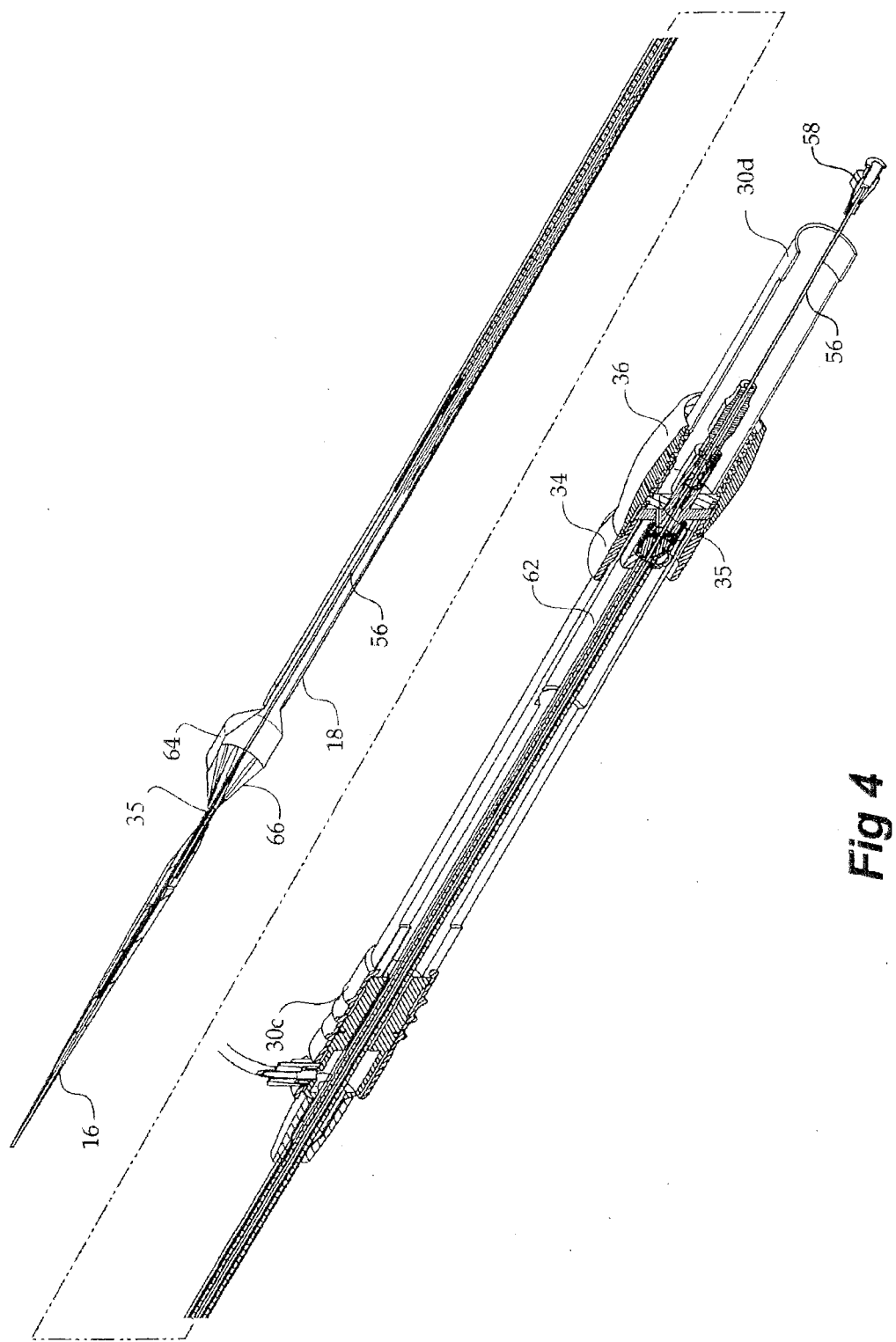
FIG. 4 shows a detailed longitudinal cross-sectional view of the embodiment of FIG. 1 with the stent graft partially deployed.

FIG. 4 shows a longitudinal cross-sectional view showing a stage in the operation of the device according to the present invention.

At the stage shown in FIG. 4 the fixed handle 34 and rotator component 36 have been gripped and the grip 30c on the release handle has been moved towards the fixed handle 34. The distal end 30d of the release handle 30 passes through the engages against the release clamp 48, as will be discussed below.

A method of retention of the proximal end of a stent graft onto a introducer is disclosed in PCT Publication WO 03/101518 entitled "Trigger Wire System for a Prosthesis Deployment Device". This feature and other features disclosed in PCT Publication WO 03/101518 could be used with the present invention and the disclosure of PCT Publication WO 03/101518 is incorporated herein by reference in its entirety into this specification.

FIGS. 5 to 9 show the various stages in deployment of a stent graft using the deployment assembly of the present invention.

In FIG. 5 a stent graft 64 is held in a retracted position in the region 24 immediately distal of the nose cone dilator 16. The stent graft 64 is held in a contracted state by the sheath 18 which extends back to the sheath hub 20. The stent graft 64 is also retained at least at its proximal end 64a to the delivery device by release or trigger wires 35 which extend back to the release clamp 48 through the lumen 39 of the pusher 38 and pusher hub 40 and then through the duct 41 in the pusher hub 40 and fastened to the release clamp 48. There can also be a similar release or trigger wire system for retention and release of the distal end 64b of the stent graft, and trigger wires for this extend back to the release clamp 48 through the lumen 39 of the pusher 38 and pusher hub 40 and then through the duct 41 in the pusher hub 40 and fastened to the release clamp 48.

Figure 9:
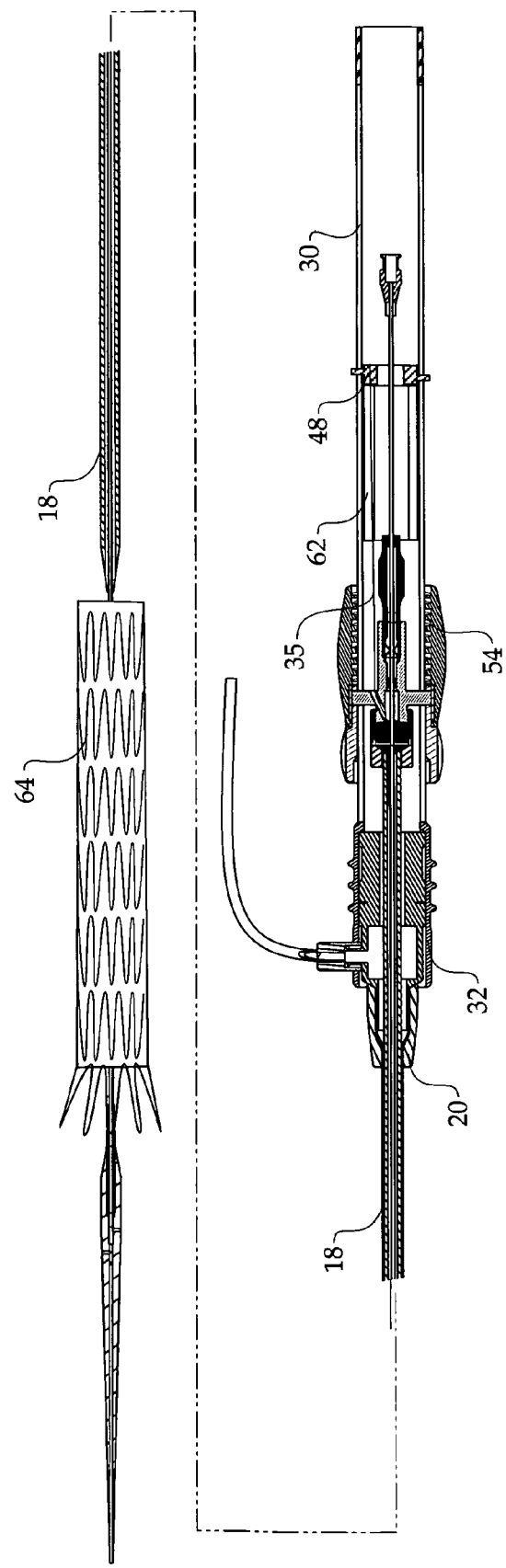

Movement of the release clamp 48 with respect to the pusher hub 40, as discussed below, will retract the trigger wires from engagement with the stent graft 64 thereby releasing the stent graft 64. It is desirable that the proximal end 64a of the stent graft 64 is released after at least two stents of the stent graft have been exposed and allowed to expand. The rotator component 36, which engages the release clamp 48, is thus arranged to be rotated only after the adjuster portion 62 has reached a stop position against the release clamp. It is desirable, also that the trigger wire retaining the distal end 64b of the stent graft 64, if present, is only released after the stent graft is fully exposed as is shown in FIG. 9. To achieve this the trigger wire is made significantly longer to extend well beyond its engagement with the stent graft 64 at the distal end 64b of the stent graft 64. This means that as the release clamp 48 continues being retracted after it has been released from the rotator component 36 stent graft 64 is released after at least two stents of the stent graft have been exposed and allowed to expand. The rotator component 36, which engages the release clamp 48, is thus arranged to be rotated only after the adjuster portion 62 has reached a stop position against the release clamp. It is desirable, also that the trigger wire retaining the distal end 64b of the stent graft 64, if present, is only released after the stent graft is fully exposed as is shown in FIG. 9. To achieve this the trigger wire is made significantly longer to extend well beyond its engagement with the stent graft 64 at the distal end 64b of the stent graft 64. This means that as the release clamp 48 continues being retracted after it has been released from the rotator component 36 and moved distally by its engagement with the adjuster portion 62 and the trigger wire for the distal end 64b of the stent graft is not released from its engagement until the sheath 18 has been fully retracted from the stent graft 64.

Both the fixed handle 34 and rotator component 36 are dimensioned so that the cylindrical body of the release handle 30 can pass through them as it is moved distally and the pusher hub 40 and the release clamp 48 are dimensioned so that the cylindrical body of the release handle 30 can pass around them. The adjuster portion 62 is dimensioned so that while it will pass around the pusher hub 40 it engages against the release clamp 48.

Partial retraction of the release handle 30 is shown in FIG. 6. At this stage the pusher hub 40 and the release clamp 48 are retained in their positions relative to the fixed handle 34 and rotator component 36 by the pins 42 and 52 respectively engaging into them. The proximally extending exposed stent 66 on the stent graft 64 is exposed by retraction of the sheath 18 and the very proximal end 64a of the stent graft 64 has also been exposed but not to a stage where the proximal end 64a of the stent graft can start to expand under the action of its self-expanding stents.

Figure 7:
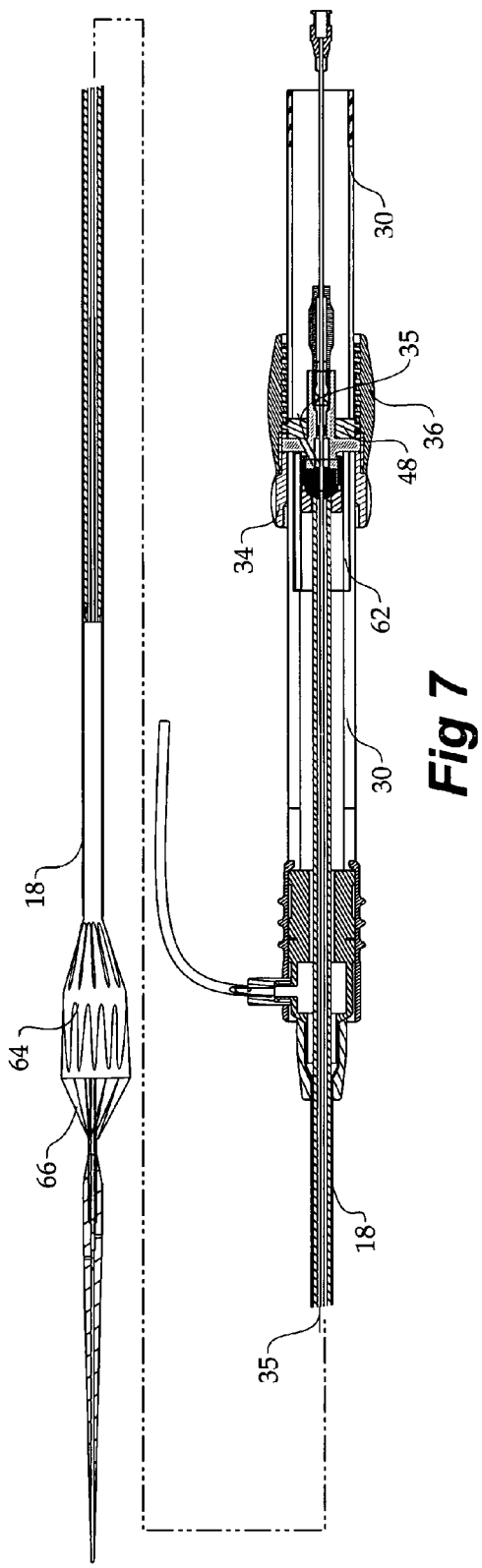

As shown in FIG. 7 continued retraction of the release handle 30 and hence also the sheath 18 with respect to the fixed handle 34 and rotator component 36 has caused the stent graft 64 to be more exposed, and the adjuster portion 62 to engage against the release clamp 48 as discussed above. This prevents further retraction. The stent graft has partially expanded under the action of its self-expanding stents. The physician can at this stage review the position of the stent graft in the vasculature and make any necessary adjustments proximally, distally or rotationally. For this purpose the stent graft may include radiopaque markers (not shown).

Figure 8:
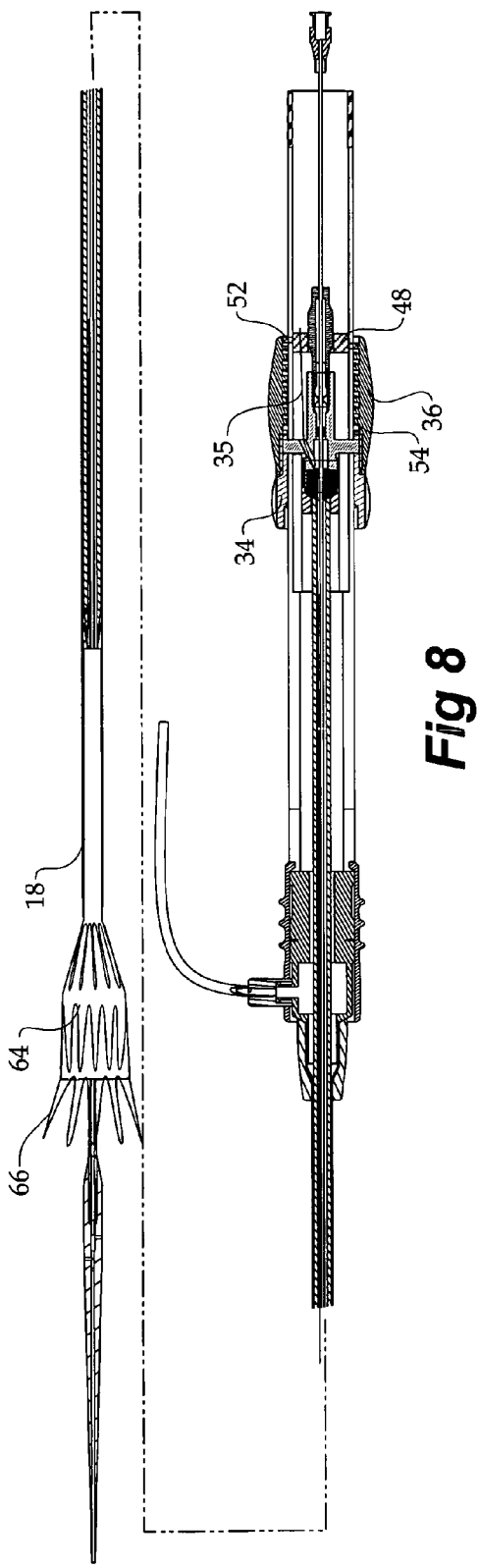

When the stent graft 64 is correctly positioned the rotator component 36 can then be rotated relative to the fixed handle 34. This will cause the release clamp 48 to move distally because the pins 52 on the release clamp are engaged into the screw thread 54 until the pins exit from the distal end of the screw thread 54. This causes the trigger wires to retract from the proximal retention so that as shown in FIG. 8 the exposed stent 66 is released and will expand as a self-expanding stent and engage against the wall of the vasculature into which it is deployed.

The adjuster portion 62 is then no longer prevented from moving by the release clamp 48 and hence the release handle 30 can be moved distally again as shown in FIG. 9. When the adjuster portion 62 again engages the release clamp 48, which is no longer constrained by the pins engaging the screw thread, it pushes the release clamp 48 distally until the sheath 18 has fully retracted off the stent graft 64. At this stage the trigger wire which releases the distal end of the stent graft, if present, is withdrawn from engagement with the stent graft.

The entire handle and deployment device assembly can then be withdrawn from the patient. Alternatively, the sheath hub 20 can be disconnected from the release handle grip 32 by separation at the bayonet connection and the sheath 18 can be left in the patient for further operations therethrough, and the handle, pusher, guide wire catheter and nose cone dilator can be retracted through the sheath.

The disclosures in U.S. patent application no. U.S. 60/964, 456, from which this application claims priority, and in the abstract accompanying this application are incorporated herein by reference.

The invention claimed is:

1. A stent graft deployment device including:
   a handle, the handle including a first part to be gripped and held by a user and a second part to be moved relative to the first part;
   a pusher on which a stent graft may be mounted at least partially disposed within the handle, the pusher comprising a hub; and a release clamp positioned on the pusher;
a sheath to cover the stent graft on the pusher, wherein the pusher is connected to the first part of the handle and the sheath is connected to the second part of the handle, whereby retraction of the second part of the handle with respect to the first part of the handle causes the sheath to be retracted from the stent graft on the pusher,
wherein the first part of the handle includes a first component to grip the pusher and a second component to grip the release clamp on the pusher, whereby movement of the second component with respect to the first component moves the release clamp on the pusher distally to release the stent graft from the pusher,
wherein a stop is disposed within an interior surface of the second part of the handle, the stop arranged to engage the release clamp on the pusher after a selected amount of movement of the second part of the handle has occurred, and
wherein the second part of the handle has longitudinal slots and an internal lumen, the pusher extends within the internal lumen longitudinally, and the pusher includes arms that extend diametrically through the longitudinal slots to engage with the first part of the handle, whereby the second part of the handle can be moved with respect to the first part of the handle.

2. A device as claimed in claim 1, wherein the release clamp on the pusher has attached thereto a trigger wire for the release of a the stent graft from the pusher, whereby movement of the release clamp pulls the trigger wire to release the stent graft from the pusher.

3. A device as claimed in claim 1, wherein the second component is rotatable with respect to the first component, whereby rotational movement of the second component causes longitudinal movement of the release clamp on the pusher.

4. A device as claimed in claim 3, wherein the second component includes a screw thread, a portion of the release clamp being engaged in the screw thread.

5. A device as claimed in claim 3, including a detent arrangement acting between the first component and the second component to allow rotation of the second component only in a selected direction.

6. A device as claimed in claim 1, wherein the second part of the handle includes a bayonet socket for a hub of the sheath.

7. A device as claimed in claim 1, wherein the second part of the handle is able to slide within the first part.

8. A device as claimed in claim 1, wherein the first part of the handle is substantially cylindrical, and wherein the second part of the handle is tubular.

9. A device as claimed in claim 1, including a first stop to prevent the second part of the handle from moving with respect to the first part of the handle in a reverse direction.

10. A stent graft deployment device, the device including:
a tubular fixed handle to be gripped and held by a user;
an elongate release handle extending through the fixed handle whereby the release handle can be moved through the fixed handle,
a pusher at least partially disposed within the tubular fixed handle and the elongate release handle, the pusher comprising a hub;
a release clamp positioned on the pusher, and
a sheath to cover a stent graft disposed on the pusher,
wherein the pusher is connected to the fixed handle and the sheath is connected to the release handle, whereby retraction of the release handle through the fixed handle causes the sheath to be retracted from the stent graft on the pusher,
wherein a stop is disposed within an interior surface of the elongate release handle, the stop arranged to engage the release clamp on the pusher after a selected amount of movement of the elongate release handle has occurred, and
wherein the release handle has longitudinal slots there along and an internal lumen, the pusher extends within the internal lumen, and wherein the pusher assembly includes arms which extend diametrically through the longitudinal slots to engage with the fixed handle, whereby the release handle can be moved with respect to the fixed handle to move the sheath with respect to the pusher.

11. A device as claimed in claim 10, wherein the fixed handle includes a grip component that grips the pusher and a rotator component that grips the release clamp on the pusher, whereby movement of the rotator component with respect to the grip component moves the release clamp on the pusher and thereby releases the stent graft.

12. A device as claimed in claim 11, wherein the release clamp on the pusher has a trigger wire for the release of the stent graft from the pusher attached thereto, whereby movement of the release clamp pulls the trigger wire to release the stent graft.

13. A device as claimed in claim 11, wherein the rotator component is able to rotate rotates with respect to the grip component, whereby rotational movement of the rotator component causes longitudinal movement of the release clamp on the pusher.

14. A device as claimed in claim 13, wherein the rotator component includes a screw thread with a portion of the release clamp engaged in the screw thread.

15. A device as claimed in claim 10, wherein the rotator component includes a screw thread with a portion of the release clamp engaged in the screw thread, wherein further retraction of the sheath is prevented until the release clamp has been moved out of engagement of the screw thread by rotation of the rotator component.

16. A device as claimed in claim 10, including a detent arrangement acting between the grip component and the rotator component of the fixed handle to allow rotation of the rotator component only in a selected direction.

17. A device as claimed in claim 10, wherein the release handle includes a bayonet socket for a hub of the sheath.

18. A device as claimed in claim 10, wherein the fixed handle includes a substantially cylindrical bore therethrough and the release handle is tubular and slides within the fixed handle.

19. A device as claimed in claim 10, including a first stop to prevent the release handle from moving through the fixed handle in a reverse direction.

20. A stent graft deployment device including:
a handle, the handle including a tubular fixed handle to be gripped and held by a user and an elongate release handle extending through the fixed handle whereby the release handle can be moved through the fixed handle;
a pusher at least partially disposed within the tubular fixed handle and the elongate release handle, the pusher comprising a hub;
a release clamp positioned on the pusher; and
a sheath to cover a stent graft on the pusher, the pusher being connected to the fixed handle and the sheath being connected to the release handle, whereby retraction of the release handle through the fixed handle causes the sheath to be retracted from a stent graft on the pusher wherein the fixed handle includes a grip component that grips the pusher and a rotator component that grips a release clamp on the pusher wherein the release clamp on the pusher has a trigger wire for the release of a stent graft from the pusher attached thereto and wherein the rotator component includes a screw thread with a portion of the release clamp engaged into the screw thread, whereby rotational movement of the rotator component causes longitudinal movement of the release clamp on the pusher thereby to pull the trigger wires, and wherein a stop is disposed within an interior surface of the elongate release handle, the stop arranged to engage the release clamp on the pusher after a selected amount of movement of the elongate release handle has occurred.

* * * * *

UNITED STATES PATENT AND TRADEMARK OFFICE
CERTIFICATE OF CORRECTION

PATENT NO. : 8,475,514 B2
APPLICATION NO. : 12/671177
DATED : July 2, 2013
INVENTOR(S) : Hartley et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 414 days.

Signed and Sealed this
Eighth Day of September, 2015

Michelle K. Lee
*Director of the United States Patent and Trademark Office*